US010513528B2

(12) United States Patent
Ponnaiah et al.

(10) Patent No.: US 10,513,528 B2
(45) Date of Patent: Dec. 24, 2019

(54) SYNTHETIC PROCESSES AND INTERMEDIATES

(71) Applicants: TAXIS PHARMACEUTICALS, INC., Monmouth Junction, NJ (US); Ravi Ponnaiah, Hyderabad (IN); Sudhakar Sunkari, Hyderabad (IN); Anil Kumar Soni, Hyderabad (IN); Savi Rami Reddy Athunuri, Hyderabad (IN); Thrisulapani Korrakuti, Hyderabad (IN); Pullarao Seelam, Hyderabad (IN)

(72) Inventors: Ravi Ponnaiah, Hyderabad (IN); Sudhakar Sunkari, Hyderabad (IN); Anil Kumar Soni, Hyderabad (IN); Savi Rami Reddy Athunuri, Hyderabad (IN); Thrisulapani Korrakuti, Hyderabad (IN); Pullarao Seelam, Hyderabad (IN); Ajit K. Parhi, Monmouth Junction, NJ (US)

(73) Assignee: Taxis Pharmaceuticals, Inc., Monmouth Junction, NJ (US)

( * ) Notice: Subject to any disclaimer, the term of this patent is extended or adjusted under 35 U.S.C. 154(b) by 0 days.

(21) Appl. No.: 16/079,469

(22) PCT Filed: Feb. 23, 2017

(86) PCT No.: PCT/US2017/019161
§ 371 (c)(1),
(2) Date: Aug. 23, 2018

(87) PCT Pub. No.: WO2017/147316
PCT Pub. Date: Aug. 31, 2017

(65) Prior Publication Data
US 2019/0048024 A1  Feb. 14, 2019

(30) Foreign Application Priority Data
Feb. 25, 2016 (IN) .............................. 201641006639

(51) Int. Cl.
C07D 513/02 (2006.01)
C07D 513/04 (2006.01)
C07C 65/24 (2006.01)
C07C 35/00 (2006.01)
C07C 43/00 (2006.01)
C07C 43/225 (2006.01)
C07D 211/62 (2006.01)
C07C 63/00 (2006.01)

(52) U.S. Cl.
CPC ............ *C07D 513/04* (2013.01); *C07C 35/00* (2013.01); *C07C 43/00* (2013.01); *C07C 43/225* (2013.01); *C07C 63/00* (2013.01); *C07C 65/24* (2013.01); *C07D 211/62* (2013.01)

(58) Field of Classification Search
CPC .................................................. C07D 513/02
See application file for complete search history.

(56) References Cited

U.S. PATENT DOCUMENTS

| 4,309,539 | A | 1/1982 | Boller et al. |
| 4,782,058 | A | 11/1988 | Griffith |
| 4,826,990 | A | 5/1989 | Musser et al. |
| 5,077,142 | A | 12/1991 | Sakon et al. |
| 5,177,067 | A | 1/1993 | Guerry et al. |
| 5,177,075 | A | 1/1993 | Suto et al. |
| 6,348,482 | B1 | 2/2002 | Hammond |
| 8,088,791 | B2 | 1/2012 | Brown et al. |
| 8,415,383 | B2 | 4/2013 | Haydon et al. |
| 8,492,414 | B2 | 7/2013 | Haydon et al. |
| 8,865,736 | B2 | 10/2014 | Brown et al. |
| 8,933,096 | B2 | 1/2015 | Lavoie et al. |
| 9,458,150 | B2 | 10/2016 | Lavoie et al. |
| 10,071,082 | B2 | 9/2018 | Lavoie et al. |
| 2002/0035090 | A1 | 3/2002 | Zeldis et al. |
| 2002/0040147 | A1 | 4/2002 | Hammond et al. |
| 2002/0055516 | A1 | 5/2002 | Miyazaki et al. |
| 2002/0077333 | A1 | 6/2002 | Dey et al. |
| 2003/0181519 | A1 | 9/2003 | Mewshaw et al. |
| 2005/0043300 | A1 | 2/2005 | Middleton et al. |
| 2006/0183943 | A1 | 8/2006 | Hu |
| 2008/0027028 | A1 | 1/2008 | Chichak |
| 2008/0300239 | A1 | 12/2008 | Adams et al. |
| 2009/0076074 | A1 | 3/2009 | Jung et al. |
| 2009/0312319 | A1 | 12/2009 | Ren et al. |
| 2010/0120810 | A1 | 5/2010 | Leblond et al. |

(Continued)

FOREIGN PATENT DOCUMENTS

| CN | 101404989 A | 4/2009 |
| DE | 4327748 A1 | 2/1995 |

(Continued)

OTHER PUBLICATIONS

Singh, et al., "Structure-Activity Relationship Studies Leading to the Identification of (2E)-3-[I-[(2,4-Dichlorophenyl)methyl]-5-fluoro-3-methyl-IH-indol-7-yl]-N-[(4,5-dicholoro-2-thienyl)sulfonyl]-2-propenamide (DG-041), a Potent and Selective Prostanoid EP3 Receptor", J. Med. Chem. 53, 18-36 (2010).

Wachall, et al., "Imidazole Substituted Biphenyls: A New Class of Highly Potent and In Vivo Active Inhibitors of P450 17 as Potential Therapeutics for Treatment of Prostate Cancer", Bioorganic and Medical Chemistry 7, 1913-1924 (1999).

Web Archive, "Enamine—Screening Compounds", http://web.archive.org/web/20070630171813/http://www.enamine.net/index.php?option=com_content&task=view&id=22&menuid=51&PHPSESSID=64a4f248f69d671a413f487bb62c4d90, Jun. 30, 2007, accessed Apr. 1, 2015.

(Continued)

*Primary Examiner* — Andrew D Kosar
*Assistant Examiner* — John S Kenyon
(74) *Attorney, Agent, or Firm* — Viksnins Harris Padys Malen LLP

(57) ABSTRACT

The invention provides synthetic processes and synthetic intermediates that can be used to prepare a compound of formula (I): or a salt thereof.

9 Claims, 2 Drawing Sheets

(56) References Cited

U.S. PATENT DOCUMENTS

| | | | |
|---|---|---|---|
| 2010/0173933 | A1 | 7/2010 | Brown et al. |
| 2012/0022061 | A1 | 1/2012 | Lavoie |
| 2012/0196891 | A1 | 8/2012 | Iwakoshi |
| 2013/0109713 | A1 | 5/2013 | Lavoie et al. |
| 2013/0116278 | A1 | 5/2013 | Lavoie |
| 2014/0135332 | A1 | 5/2014 | Haydon et al. |
| 2014/0350024 | A1 | 11/2014 | Lavoie et al. |
| 2015/0011559 | A1 | 1/2015 | Lavoie et al. |
| 2015/0031694 | A1 | 1/2015 | Lavoie et al. |
| 2015/0133465 | A1 | 5/2015 | Lavoie et al. |
| 2015/0307517 | A1* | 10/2015 | Lavoie .............. C07D 413/12 514/253.04 |

FOREIGN PATENT DOCUMENTS

| | | | |
|---|---|---|---|
| EP | 0136745 | A2 | 4/1985 |
| EP | 0719764 | A1 | 7/1996 |
| EP | 1078920 | A1 | 2/2001 |
| EP | 1724262 | A1 | 11/2006 |
| JP | 2012051885 | A | 3/2012 |
| WO | 1992019242 | A1 | 11/1992 |
| WO | 2002044127 | A1 | 6/2002 |
| WO | 2003018017 | A1 | 3/2003 |
| WO | 2003078397 | A1 | 9/2003 |
| WO | 2003099274 | A1 | 12/2003 |
| WO | 2004000814 | A1 | 12/2003 |
| WO | 2004005472 | A2 | 1/2004 |
| WO | 2004018414 | A2 | 3/2004 |
| WO | 2004041210 | A2 | 5/2004 |
| WO | 2004073709 | A1 | 9/2004 |
| WO | 2004087145 | A2 | 10/2004 |
| WO | 2005075428 | A1 | 8/2005 |
| WO | 2005097100 | A2 | 10/2005 |
| WO | 2006067048 | A1 | 6/2006 |
| WO | 2006105289 | A1 | 10/2006 |
| WO | 2007107758 | A1 | 9/2007 |
| WO | 2007148093 | A1 | 12/2007 |
| WO | 2008016596 | A2 | 2/2008 |
| WO | 2009037485 | A1 | 3/2009 |
| WO | 2009040507 | A1 | 4/2009 |
| WO | 2009074810 | A1 | 6/2009 |
| WO | 2009074812 | A1 | 6/2009 |
| WO | 2009081892 | A1 | 7/2009 |
| WO | 2010127307 | A1 | 11/2010 |
| WO | 2011112435 | A1 | 9/2011 |
| WO | 2011156626 | A1 | 12/2011 |
| WO | 2012142671 | A1 | 10/2012 |
| WO | 2014074932 | A1 | 5/2014 |
| WO | WO-2014074932 | A1 * | 5/2014 ........... C07D 413/12 |

OTHER PUBLICATIONS

Wigbers, et al., "Synthesis, Structures, and Aggregation Properties of N-Acylamidines", Eur. J. Org. Chem., 861-877 (2011).
Wu, et al., "Regulatory perspectives of Type II prodrug development and time-dependant toxicity management: Nonclinical Pharm/Tox analysis and the role of comparitive toxicology", Toxicology 236, 1-6 (2007).
Yaeko, et al., "Studies on the Constituents of Bocconia Cordata. IV. Transformation of sanguinarine into bocconine", XP002570841, Chemical Abstracts Service, Database accession No. 1992:129332, abstract, Journal of Heterocyclic Chemistry, 28(8), 1841-1843 (1991).
Yamaguchi, et al., "Utilization of Protopine and Related Alkaloids. XIV. Oxidation of the Photo-adduct of 1-Oxoanhydromethylberberine with Nitrosobenzene, and Synthesis of Ring C-Substituted Benzo[c]phenanthridines", Chem. Pharm. Bull., 31(5), 1601-1611 (1983).
Akiba, et al., "Preparation of 13-Substituted 8H-Dibenzo[a,g]quinolizin-8-onces by Intramolecular Wittig-Horner Reaction of Dialkyl 2-(o-Acyl-benzoyl)-1,2-dihydro-1-isoquinolylphosphonates", Bull. Chem. Soc. Japan, 57 (8), 2199-2192 (1984).

Augstein, et al., "Synthesis of 11-Hydroxy-2,3,9,10-tetramethoxy-5-6-13,13a-tetrahydro-8H-dibenzo[a,g]quinolizine. A Contribution of the Structure of Stepharotine", Stepharotine, vol. 34, No. 5, 3149-1352 (1969).
Bayer, et al., "Pyridyl-substituierte Tetralonderivate: Eine neue Klasse nichtsteroidaler Aromatase-Inhibitoren", Arch. Pharm. 324, 815-820 (1991). [English Abstract].
Bedi, et al., "Synthesis and biological activity of novel antibacterial quinazolines", Bioorganic & Medical Chemistry Letters 14, 5211-5213 (2004).
Beilstein, Database Beilstein Institute for Organic Chemistry, XP002591900, Database Accession No. 3837583 (BNR) abstract (1930).
Beilstein, Database Beilstein Institute for Organic Chemistry, XP002591901, Database Accession No. 3834367 (BRN) abstract (1918).
Beuria, et al., "Sanguinarine Blocks Cytokinesis in Bacteria by Inhibiting FtsZ Assembly and Bundling", Biochemistry, 44, 16584-16593 (2005).
Bild, et al., "Discovery of Inhibitors of MCF-7 Tumor Cell Adhesion to Endothelial Cells and Investigation on their Mode of Action", Arch. Pharm. Pharm. Med. Chem., 337, 687-694 (2004).
Chemical Abstract, "Enamine", Database STN, RN 1375188-04-7 for N-(methylsulfonyl)-3-[(2-methyl-4-thiazolyl)methoxy]-Benzamide, Entered STN: Jun. 5, 2012.
Chemical Abstracts, STN Registry Database Record for RN 338394-05-1, Entered May 25, 2001.
Chen, et al., "Synthesis and Antibacterial Evaluation of Certain Quinolone Derivatives", J. Med. Chem. 44, 2374-2377 (2001).
Cole, et al., "Potential Tumor-Selective Nitroimidazolylmethyluracil Prodrug Derivatives: Inhibitors of the Angiogenic Enzyme Thymidine Phosphorylase", J. Med. Chem. 46, 207-209 (2003).
Czaplewski, et al., "Antibacterial alkoxybenzamide inhibitors of the essential bacterial cell division protein FtsZ", Bioorganic & Medicinal Chemistry Letters 19, 524-527 (2009).
Database Registry, Chemical Abstracts Service, Registry No. 1211090-40-2, entered Mar. 17, 2010.
Database Registry, Chemical Abstracts Service, Registry Nos. 1177870-80-2, entered Aug. 30, 2009; 1024284-46-5, entered Jun. 1, 2008; 1022864-66-9, entered May 27, 2008; 1022446-60-1, 1022368-26-8, entered May 25, 2008; 1022127-38-3 entered May 23, 2008.
Database Registry [Online], Chemical Abstracts Service, XP002570845, Database accession No. 1043564-34-0/RN, abstract (2008).
Denes, et al., "The chemistry of sanguinarine", XP002570844, Chemical Abstracts Service, Database accession No. 1960:91836, abstract, Magyar Kemiai Folyoirat, 64, 125-130 (1958).
Dorwald, "Side Reactions in Organic Synthesis: A Guide to Successful Synthesis Design", Wiley-VCH Verlag GmbH & Co. KGaA, Wienheim, 32 pages (2005).
Dyke, et al., "The Chemistry of Cryptopine—I The Epicryptopines", Tetrahedron, vol. 24, No. 3, 1455-1465 (1968).
Dyke, et al., "The Chemistry of Cryptopine—II The Pseudocryptopine Chloride", Tetrahedron, vol. 25, 5375-5381 (1969).
Dykhuizen, "Santa Rosalia revisited: Why are there so many species of Bacteria?", Antoine van Leeuwenhock, 73, 25-33 (1998).
Elsen, et al., "Mechanism of Action of the Cell-Division Inhibitor PC190723: Modulation of FtsZ Assembly Cooperativity", Journal of American Chemical Society 134, 12342-12345 (2012).
Foroumadi, et al., "Synthesis and in vitro antibacterial evaluation of N-[5-(5-nitro-2-thienyl)-1,3,4-thiadiazole-2-yl] piperazinyl quinolones", European Journal of Medicinal Chemistry, 38, 851-854 (2003).
Gopinath, et al., "Dehydrogenation cyclization of 2-aryl-l-tetralone oxime acetates", XP002570843, Chemical Abstracts Service, Database accession No. 1960:23123, abstract, Current Science, 28, 241-242 (1959).
Haydon, et al., "Creating an antibacterial with in vivo efficacy: synthesis and characterization of potent inhibitors of the bacterial cell division protein FtsZ with improved pharmaceutical properties", J. Med. Chem 53, 3927-3936 (2010).
Huecas, et al., "Protein Structure and Folding: The Interactions of Cell Division Protein FtsZ with Guanine Nucleotides", J. Biol. Chem. 282, 37515-37528 (2007).

(56) References Cited

OTHER PUBLICATIONS

Huttunen, et al., "Prodrugs—An Efficient Way to Breach Delivery and Targeting Barriers", Current Topics in Medicinal Chemistry, 11, 2265-2287 (2011).

Ishii, et al., "Studies on the Chemical Constituents of Rutaceous Plants. LV. 1. The Development of a Versatile Method for the Synthesis of Antitumor-Active Benzo[c]phenanthridine Alkaloids. (5)1. A New Method for Quaternization of the Benzo[c]phenanthridine Nucleus", Chem. Pharm. Bull., 32(8), 2984-2994 (1984).

Ito, et al., "A medium-term rat liver bioassay for rapid in vivo detection of carcinogenic potential of chemicals", Cancer Sci, vol. 94 (1), 3-8 (2003).

Jackson, et al., "Non-Steroidal Aromatase Inhibitors Based on a Biphenyl Scaffold: Synthesis, in vitro SAR, and Molecular Modelling", Chem Med Chem 3, 603-618 (2008).

Jaiswal, et al., "Totarol inhibits bacterial cytokinesis by perturbing the assembly dynamics of FtsZ", Biochemistry, vol. 46(14), 4211-4220 (2007).

Kaul, et al., "A Bactericidal Guanidinomethyl Biaryl That Alters the Dynamics of Bacterial FtsZ Polymerization", Journal of Medicinal Chemistry, 55, 10160-10176 (2012).

Kaul, et al., "A FtsZ-Targeting Benzamide Prodrug with Improved Pharmacokinetics and Enhanced In Vivo Efficacy against Methicillin-Resistant *Staphylococcus aureus*", Antimicrobial Agents and Chemotherapy 59, 1-9 (2015).

Kaul, et al., "An FtsZ-Targeting Prodrug with Oral *Antistaphylococcal* Efficacy In Vivo", Antimicrobial Agents and Chemotherapy 57(12), 5860-5869 (2013).

Kaul, et al., "Enterococcal and *streptococcal* resistance to PC190723 and related coumpounds: Molecular insights from a FtsZ mutational analysis", Biochimie 95, 1880-1887 (2013).

Kaul, et al., "Pharmacokinetics and in vivo *antistaphylococcal* efficacy of TXY 541, a 1-methylpiperidine-4-carboxamide prodrug of PC190723", Biochemical Pharmacology 86, 1699-1707 (2013).

Leroux, et al., "N-(4-Biphenylmethyl)imidazoles as Potential Therapeutics for the Treatment of Prostate Cancer: Metabolic Robustness Due to Fluorine Substitution?", Helvetica Chimica Acta, vol. 86, 2671-2686 (2003).

Moellering, "MRSA: the first half century", J Antimicrob Chemother 67, 4-11 (2012). Advance Access publication Oct. 2011.

Musser, et al., "N-[(Arylmethoxy)phenyl] Carboxylic Acids, Hydroxamic Acids, Tetrazoles, and Sulfonyl Carboxamides. Potent Orally Active Leukotriene D, Antagonists of Novel Structure", J. Med. Chem. vol. 33, 240-245 (1990).

Nicolson, et al., "Potentiation of methicillin activity against methicillin-resistant *Staphylococcus aureus* by diterpenes", FEMS Microbiology Letters 179, 233-239 (1999).

Okudaira, et al., "A Study of the Intestinal Absorption of an Ester-Type Prodrug, ME3229, in Rats: Active Efflux Transport as a Cause of Poor Bioavailability of the Active Drug", Journal of Pharmacology and Experimental Therapeutics, vol. 294(2), 580-587 (2000).

Patent Cooperation Treaty, International Searching Authority, Search Report and Written Opinion for PCT/US2017/019161, 6 pages, May 16, 2017.

Pitt, et al., "Heteroaromatic Rings of the Future", J. Med. Chem. 52, 2952-2963 (2009).

Pozharskii, et al., "Heterocycles in Life and Society. An Introduction to Heterocyclic Chemistry and Biochemistry and the Role of Heterocycles in Science, Technology, Medicine and Agriculture", Wiley, pp. 1-6 (1997).

Roesch, et al., "Synthesis of isoquinolines and pyridines by the palladium-catalyzed iminoannulation of internal alkynes", J. Org. Chem. 66, 8042-8051 (2001).

Sanders, et al., "Selective Cytotoxicity of Topoisomerase-Directed Protoberberines against Glioblastoma Cells", Biochemical Pharmacology, vol. 56, 1157-1166 (1998).

Schonenberger, "Synthesis and Pharmacological test of N-(3'-Methoxy-benzamidomethyl)-D-norephedrine and Analogous Compounds", Arch. Pharm 309, 289-301 (1976). [English Abstract].

Sethi, et al., "Enzyme Inhibition VIII: Mode of Inhibition of Reverse Transcriptase Activity of Analogues, Isomers, and Related Alkaloids of Coralyne", Journal of Pharmaceutical Sciences, vol. 74 (8), 889-891 (1985).

Shaheen, et al., "A microbial aetiology of acne: what is the evidence?", British Journal of Dermatology 165, 474-485 (2011).

Silverman, "The Organic Chemistry of Drug Design and Drug Action", 2nd Edition, pp. 17-23 (2008).

\* cited by examiner

SYNTHETIC PROCESSES AND INTERMEDIATES

RELATED APPLICATIONS

This application claims priority to Indian Application No. 201641006639 filed on 25 Feb. 2016. The entire contents of the foregoing are incorporated herein by reference.

BACKGROUND OF THE INVENTION

International Patent Application Publication Number WO 2014/074932 reports a series of soluable compounds that are useful as antibiotic agents. One of these compounds, the compound of formula (I):

(I)

is currently being evaluated for potential use as an antibacterial agent in humans.

Currently there is a need for improved synthetic processes and new synthetic intermediates that can be used to prepare commercial quantities of the compound of formula (I).

SUMMARY OF THE INVENTION

The invention provides synthetic processes and synthetic intermediates that can be used to prepare a compound of formula (I) or a salt thereof. These processes and intermediates allow commercial quantities of the compound to be prepared in a cost effective and enviornmentally acceptable manner. Accordingly, these processes and intermediates will facilitate the commercial development of the compound of formula (I).

In one embodiment the invention provides a method for preparing a compound of formula (I):

(I)

comprising reacting a phenol of formula e:

e with a chloride of formula h:

h to provide the compound of formula (I).

In one embodiment the invention provides a method for preparing a chloride of formula h by reacting the amino pyridine of formula g:

g with chloroacetic acid:

to provide the chloride of formula h.

In one embodiment the invention provides a method for preparing an amino pyridine of formula g by converting a corresponding nitro pyridine of formula f:

f to the amino pyridine of formula g.

In one embodiment the invention provides a method for preparing a nitro pyridine of formula f by reacting 2-chloro-3-nitro-5-(trifluoromethyl)pyridine with thiourea to provide the nitro pyridine of formula f.

In one embodiment the invention provides a method for preparing a phenol of formula e:

e

Comprising deprotecting the corresponding benzyl ether of formula d:

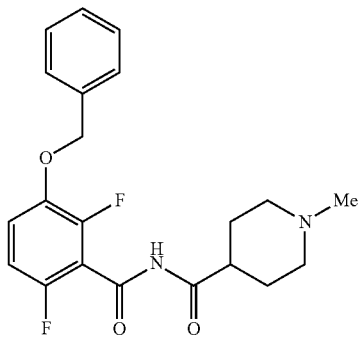

to provide the phenol of formula e.

In one embodiment the invention provides a method for preparing a benzyl ether of formula d:

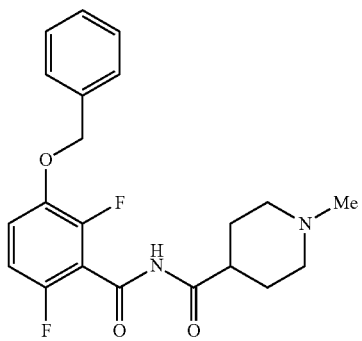

by coupling an acid chloride of formula i or a salt thereof:

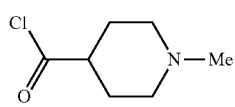

with an amide of formula c:

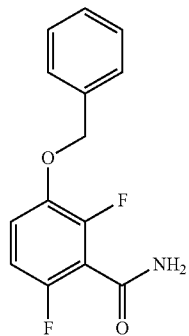

to provide the benzyl ether of formula d.

In one embodiment the invention provides a method for preparing an amide of formula c by converting an acid of formula b:

to the amide of formula c.

In one embodiment the invention provides a method for preparing an acid of formula b by converting a compound of formula a:

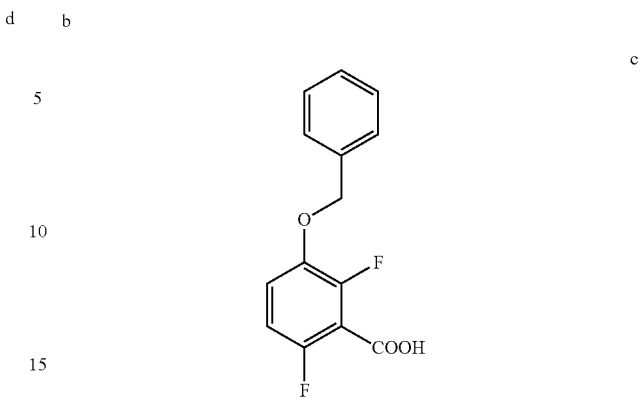

to the acid of formula b.

In one embodiment the invention provides a method for preparing a compound of formula a by converting a 2,4-difluorophenol to the compound of formula a.

In one embodiment the invention provides a method for preparing a compound of formula (I):

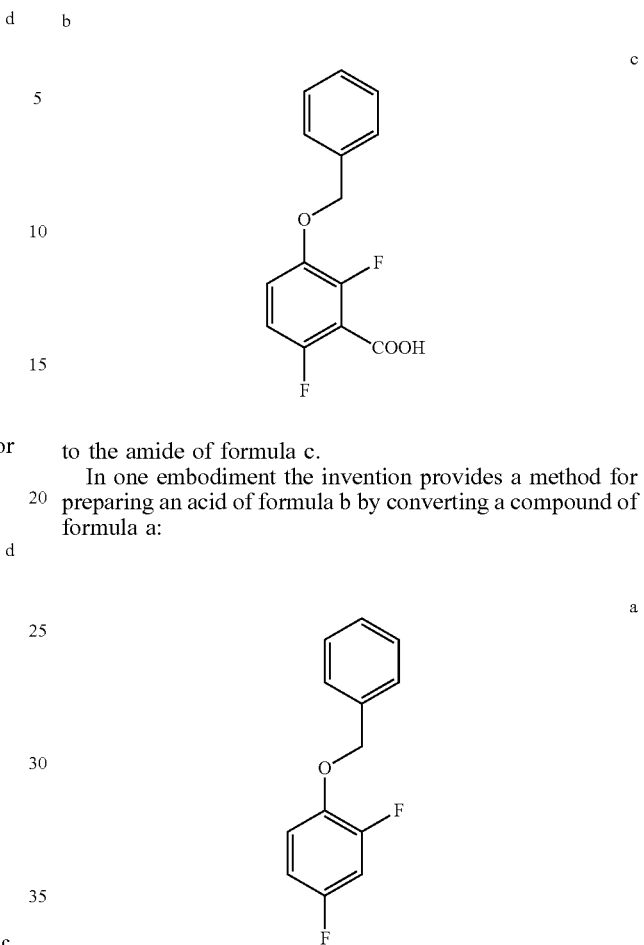

comprising reacting a phenol of formula j:

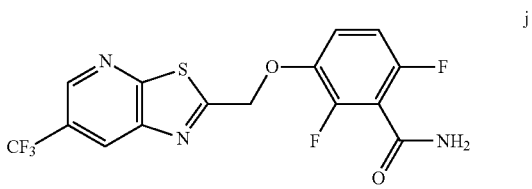 [SMILES: NC(=O)c1c(F)ccc(OCc2nc3cc(C(F)(F)F)cnc3s2)c1F]

with an acid chloride of formula:

[Structure 5: 1-methylpiperidine-4-carbonyl chloride hydrochloride]

to provide the compound of formula (I).

In one embodiment the invention provides a method for preparing a compound of formula j:

[Structure j: 6-(trifluoromethyl)thiazolo[5,4-b]pyridin-2-yl-methoxy substituted difluorobenzamide]

comprising reacting a chloride of formula h:

[Structure h: 2-(chloromethyl)-6-(trifluoromethyl)thiazolo[5,4-b]pyridine]

with a compound of formula:

[Structure: 3-hydroxy-2,6-difluorobenzamide]

to provide the compound of formula j.

In one embodiment the invention provides a compound selected from:

[Structure a: benzyloxy-2,4-difluorobenzene]

[Structure b: 3-(benzyloxy)-2,6-difluorobenzoic acid]

[Structure c: 3-(benzyloxy)-2,6-difluorobenzamide]

[Structure d: 3-(benzyloxy)-2,6-difluoro-N-(1-methylpiperidine-4-carbonyl)benzamide]

[Structure e: 3-hydroxy-2,6-difluoro-N-(1-methylpiperidine-4-carbonyl)benzamide] and

[Structure h: 2-(chloromethyl)-6-(trifluoromethyl)thiazolo[5,4-b]pyridine]

and salts thereof.

DETAILED DESCRIPTION

Figure 1:
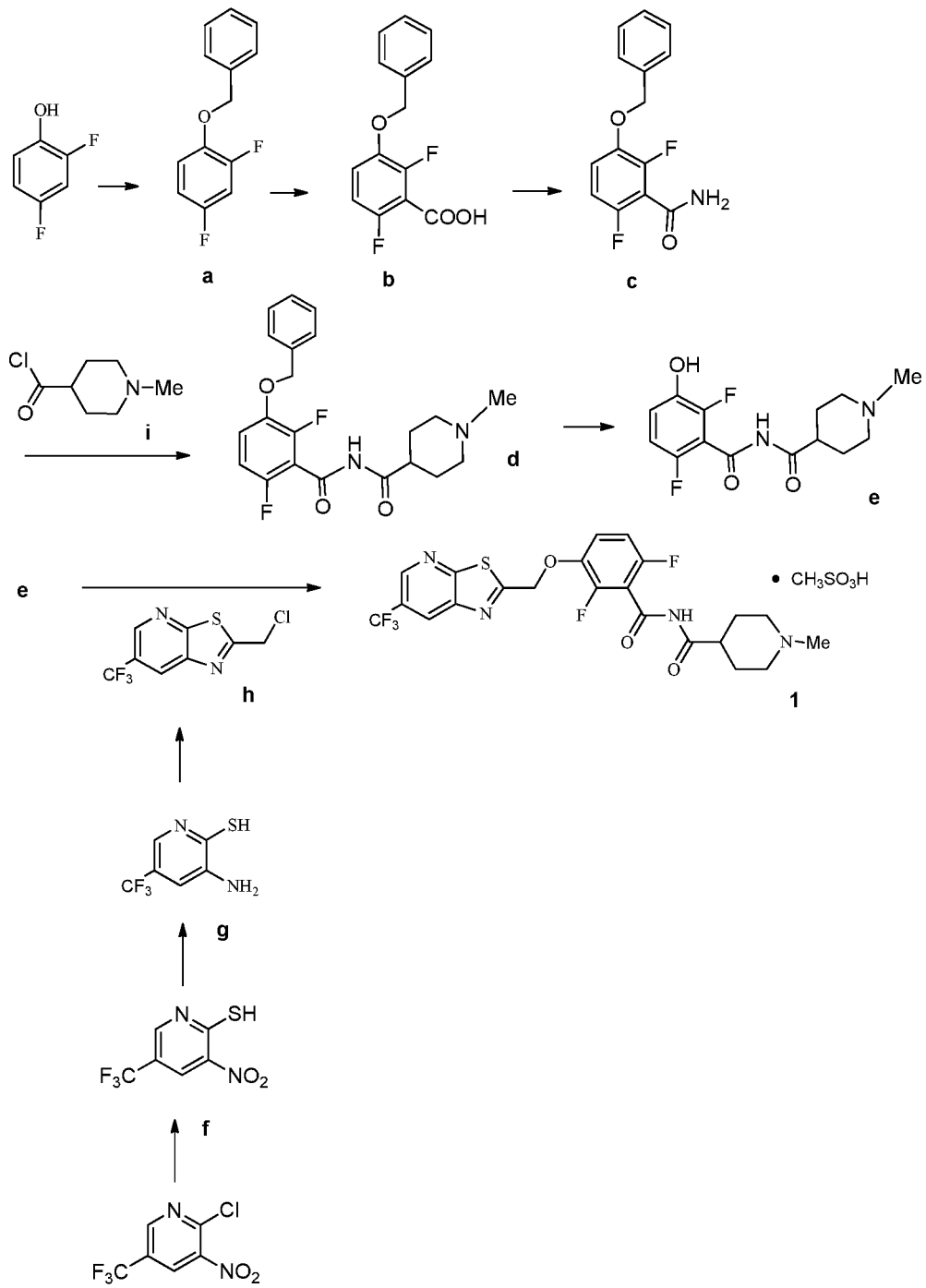
FIG. 1 illustrates synthetic routes of the invention and synthetic intermediates of the invention.
Figure 2:
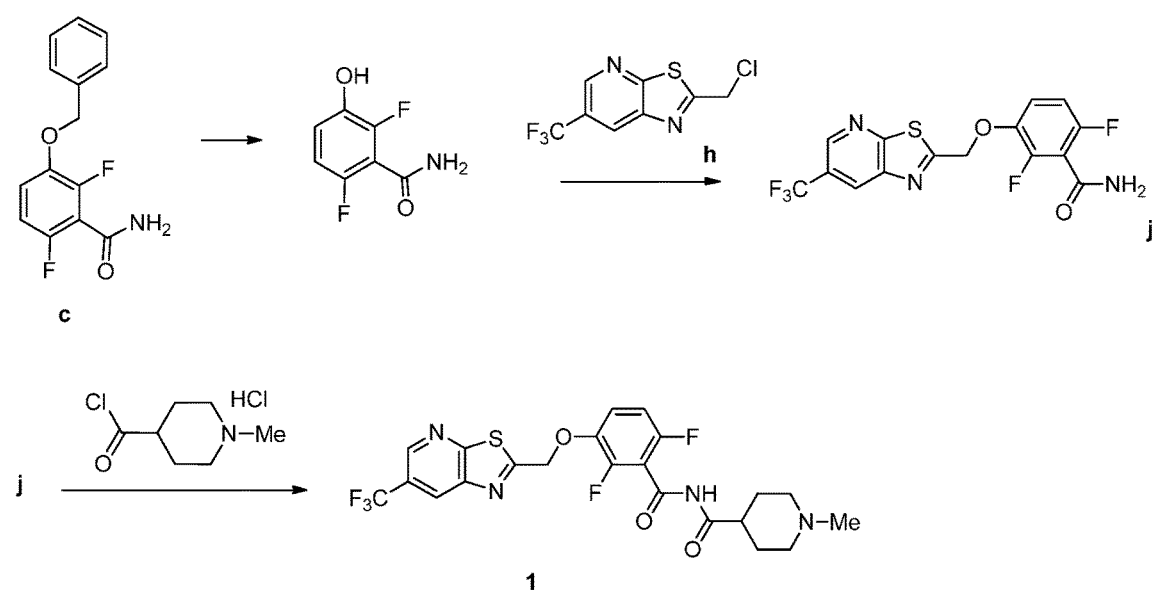
FIG. 2 illustrates synthetic routes of the invention and synthetic intermediates of the invention.

In one embodiment the invention provides a method for preparing a compound of formula (I):

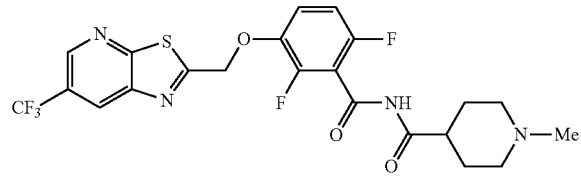

(I)

comprising reacting a phenol of formula e:

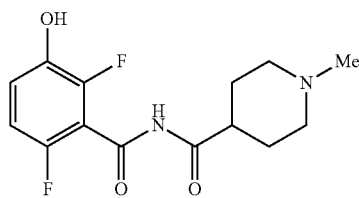

e with a chloride of formula h:

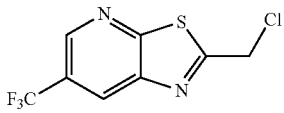

h to provide the compound of formula (I). The reaction can typically be carried out at a temperature in the range of about 25° C. to about 30° C. or in the range of about 20° C. to about 35° C. in a polar solvent. Suitable solvents include polar solvents (e.g. DMF or DMSO) and mixtures thereof. Suitable bases include inorganic bases, such as hindered bases (e.g. Potassium carbonate, sodium carbonate). For the salt preparation, use acid include methane sulfonic acid, oxalic acid and tartaric acid. In one embodiment the reaction can be carried out at a temperature in the range of about 25° C. to about 30° C. or in the range of about 20° C. to about 35° C.

In one embodiment the invention provides a method for preparing a chloride of formula h by reacting the amino pyridine of formula g:

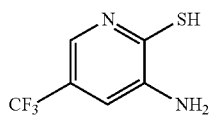

g with chloroacetic acid:

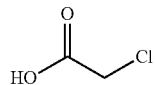

to provide the chloride of formula h. The reaction can typically be carried out at a temperature in the range of about 50° C. to about 55° C. or in the range of about 45° C. to about 60° C. in a polar solvent. Suitable solvents include ethyl acetate, chlorinated hydrocarbons (e.g. dichloromethane), and aromatic hydrocarbons (e.g. toluene), and mixtures thereof. In one embodiment the reaction can be carried out at a temperature in the range of about 50° C. to about 55° C. or in the range of about 45° C. to about 60° C.

In one embodiment the invention provides a method for preparing an amino pyridine of formula g by converting a corresponding nitro pyridine of formula f:

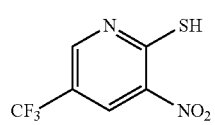

f to the amino pyridine of formula g. The reaction can typically be carried out at a temperature in the range of about 65° C. to about 70° C. or in the range of about 60° C. to about 80° C. in a polar solvent. Suitable solvents include ethyl acetate and mixtures thereof. Suitable reducing agents include iron/acetic acid, zinc/ammonium chloride. In one embodiment the reaction can be carried out at a temperature in the range of about 65° C. to about 70° C. or in the range of about 60° C. to about 80° C.

In one embodiment the invention provides a method for preparing a nitro pyridine of formula f by reacting 2-chloro-3-nitro-5-(trifluoromethyl)pyridine with thiourea to provide the nitro pyridine of formula f. The reaction can typically be carried out at a temperature in the range of about 50° C. to about 55° C. or in the range of about 40° C. to about 60° C. in a protic solvent. Suitable solvents include protic solvent (e.g. methanol, isopropyl alcohol or ethanol), and mixtures thereof. In one embodiment the reaction can be carried out at a temperature in the range of about 50° C. to about 55° C. or in the range of about 40° C. to about 60° C.

In one embodiment the invention provides a method for preparing a phenol of formula e:

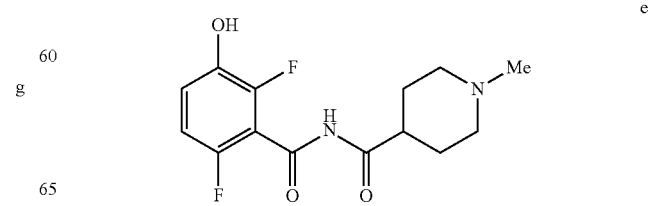

e comprising de-protecting the corresponding benzyl ether of formula d:

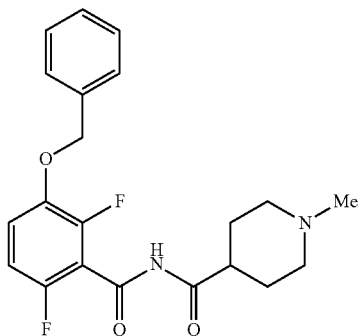

d to provide the phenol of formula e. The reaction can typically be carried out at a temperature in the range of about 25° C. to about 30° C. or in the range of about 20° C. to about 35° C. in a polar solvent. Suitable solvents include polar solvents (e.g. DMF or DMSO), protic solvents (e.g. methanol, ethanol) and mixtures thereof. Suitable reducing reagents include Pd/C, Pd(OH)$_2$ and ceric ammonium nitrate. In one embodiment the reaction can be carried out at a temperature in the range of about 25° C. to about 30° C. or in the range of about 20° C. to about 35° C.

In one embodiment the invention provides a method for preparing a benzyl ether of formula d:

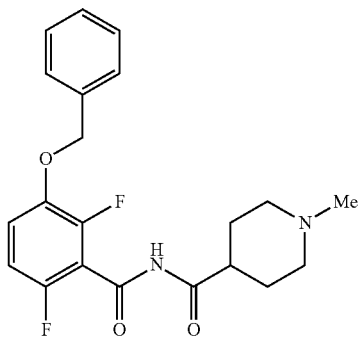

d by coupling an acid chloride of formula i or a salt thereof:

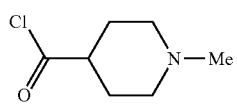

i with an amide of formula c:

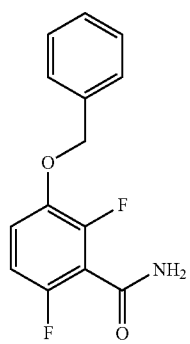

c to provide the benzyl ether of formula d. The reaction can typically be carried out at a temperature in the range of about 25° C. to about 30° C. or in the range of about 0° C. to about 35° C. in a polar solvent. Suitable solvents include hydrocarbons (e.g. THF), polar solvents (e.g. DMF, DMSO), and mixtures thereof. Suitable bases include inorganic bases (e.g. NaH). In one embodiment the reaction can be carried out at a temperature in the range of about 25° C. to about 30° C. or in the range of about 0° C. to about 35° C.

In one embodiment the invention provides a method for preparing an amide of formula c by converting an acid of formula b:

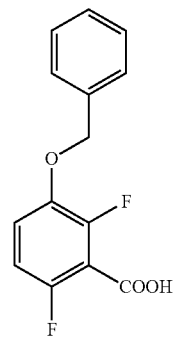

b to the amide of formula c. The reaction can typically be carried out at a temperature in the range of about −75° C. to about 0° C. or in the range of about −80° C. to about 0° C. in a polar solvent. Suitable solvents include ethers (e.g. THF, diethyl ether and MTBE), and mixtures thereof. Suitable bases include n-BuLi. In one embodiment the reaction can be carried out at a temperature in the range of about −75° C. to about 0° C. or in the range of about −80° C. to about 0° C.

In one embodiment the invention provides a method for preparing an acid of formula b by converting a compound of formula a:

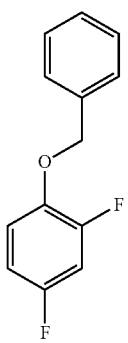 [SMILES: Fc1ccc(OCc2ccccc2)c(F)c1]

a to the acid of formula b. The reaction can typically be carried out at a temperature in the range of about 25° C. to about 30° C. or in the range of about 20° C. to about 40° C. in a polar solvent. Suitable solvents include polar solvents (e.g. DMF, THF), and mixtures thereof. Suitable bases include aqueous ammonia. In one embodiment the reaction can be carried out at a temperature in the range of about 25° C. to about 30° C. or in the range of about 20° C. to about 40° C.

In one embodiment the invention provides a method for preparing a compound of formula a by converting a 2,4-difluorophenol to the compound of formula a. The reaction can typically be carried out at a temperature in the range of about 55° C. to about 60° C. or in the range of about 40° C. to about 65° C. in a polar solvent. Suitable solvents include polar solvents (e.g. acetone, acetonitrile), protic solvents (e.g. methanol, ethanol) and mixtures thereof. Suitable bases include inorganic bases such as potassium carbonate, sodium carbonate. In one embodiment the reaction can be carried out at a temperature in the range of about 55° C. to about 60° C. or in the range of about 40° C. to about 65° C. In one embodiment the invention provides a method for preparing a compound of formula (I):

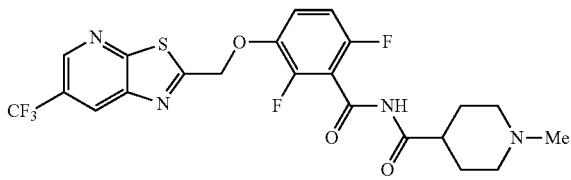
(I)

comprising reacting an amide of formula j:

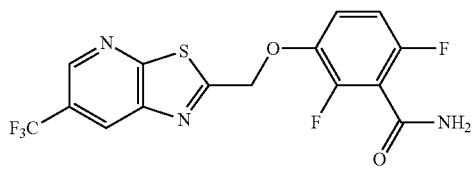
j with an acid chloride of formula:

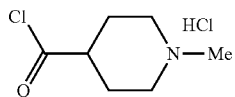

to provide the compound of formula (I). The reaction can typically be carried out at a temperature in the range of about 0° C.–50° C. in a polar solvent. Suitable solvents include THF, DMF, ACN, DMSO, and mixtures thereof. Suitable bases include amine bases, such as hindered amine bases (e.g. N,N-diisopropyl-N-ethylamine), inorganic bases such as NaH, KH, NaOH, KOH, NaO$^t$Bu In one embodiment the reaction can be carried out at a temperature in the range of about 0° C.-rt in DMF with NaH as base.

In one embodiment the invention provides a method for preparing a compound of formula j:

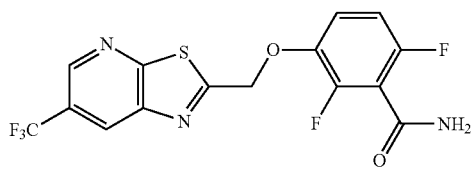
j comprising reacting a chloride of formula h:

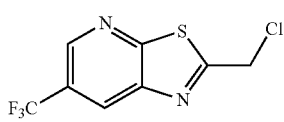
h with a compound of formula:

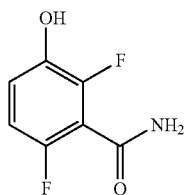

to provide the compound of formula j. The reaction can typically be carried out at a temperature in the range of about 45° C. to about 50° C. or in the range of about 40° C. to about 60° C. in a polar solvent. Suitable solvents include polar solvents (e.g. DMF, THF) and mixtures thereof. Suitable bases include inorganic bases, such as sodium bicarbonate. In one embodiment the reaction can be carried out at a temperature in the range of about 45° C. to about 50° C. or in the range of about 40° C. to about 60° C.

The invention will now be illustrated by the following non-limiting examples.

EXAMPLES

Example 1 Preparation of Compound

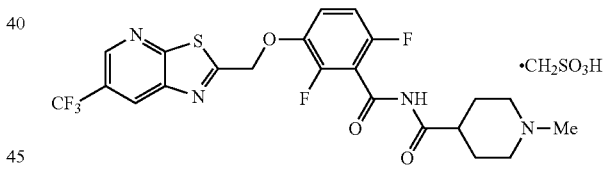

Preparation of TXA709. Mesylate: The TXA709 free base was dissolved in THF (1.5 L, 7.5 vol) and added Methane sulfonic acid (66 g, 686.78 mmol) at 35-40° C. The contents were stirred for 16 h at 25-30° C., cooled to 0-5° C. and stirred for 1 h and filtered to give crude as brown solid.
Purification of TXA709 Mesylate: To the solution of crude (TXA709 free base) dissolved in Acetone:Methanol (5.5: 7.0) mixture (2.5 L, 12.5 vol) at 55-65° C., activated carbon (0.5 g) was added, stirred for 15 min and filtered through Hyflo in hot condition. The filtrate was cooled to 25-30° C., followed by further cooling to 0-5° C. The contents were stirred for 2 h, filtered and dried at 50-55° C. for 8 h to give pure product of TXA709.Mesylate as light brown solid. (114.0 g, 27.89% yield). $^1$H NMR (300 MHz, DMSO-d$_6$) δ: 11.74 (bs, 1H), 9.07 (s, 1H), 8.95 (s, 1H), 7.50-7.58 (m, 1H), 7.17-7.24 (m, 1H), 5.81 (s, 2H), 3.45-3.50 (d, 2H), 2.91-3.02 (m, 2H), 2.77-2.84 (d, 4H), 2.31 (s, 3H), 2.04-2.08 (d, 2H), 1.65-1.77 (m, 2H). MS: 515.08 (M+1).
Preparation of TXA709. Free Base: To a 10 L 4-neck round bottom flask equipped with a mechanical stirrer, charged N-[(2,6-Difluoro-3-hydroxyphenyl)carbonyl]-1-methyl piperidine-4-carboxamide (200 g, 670.49 mmol), DMF (5.0 L, 25 vol.), Potassium carbonate (102 g, 738.06 mmol) and 2-(Chloromethyl)-6-(trifluoromethyl)[1,3]thiazolo[5,4-b]pyridine (254 g. 1005.38 mmol.) under nitrogen atmosphere. The reaction mixture was stirred for 6 h at 25-30° C. Monitored the reaction conversion by HPLC. After the reaction completion, reaction mixture mass was quenched with 1N HCl and adjust the PH to 7.0 to 7.5. The precipitated solid was filtered and washed with water to give a brown solid. The crude solid obtained was purified with water (2.0 L, 10 vol.) and dried for 18 h at 60-65° C.

The intermediate compound N-[(2,6-Difluoro-3-hydroxyphenyl)carbonyl]-1-methylpiperidine-4-carboxamide used in Example 1 was prepared as follows.

a. Preparation of 1-(Benzyloxy)-2,4-difluorobenzene

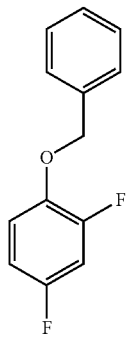

To a 5.0 L 4-neck round bottom flask equipped with a mechanical stirrer, was charged 2,4-Difluorophenol (500 g, 3843.49 mmol), Benzyl bromide (665 g, 3880 mmol), Potassium carbonate (635 g, 4590 mmol) and Acetone (3000 mL, 6.0 vol.) at 25-30° C. The contents were stirred for 1 h at 55-60° C. The reaction completion was monitored by HPLC After completion of the reaction, distilled the acetone completely at below 50° C. and cooled to 25-30° C. Water (5.0 L, 10.0 vol.) was added slowly at 25-30° C. and further cooled to 0-10° C. The contents were stirred for 1 h and the solid was filtered & dried to give a crude solid. The crude was washed with water (2.5 L, 5.0 vol.) and 10% Isopropyl alcohol:Water Mixture (2.5 L, 5.0 vol.) at 25-30° C. & dried at 30-35° C. under reduced pressure for 8 h to give pure product as white solid (805 g, 95.26% yield). $^1$H NMR (300 MHz, DMSO-$d_6$) δ: 7.23-7.47 (m, 7H), 6.97-7.05 (m, 1H), 5.16 (s, 2H).

b. Preparation of 3-(Benzyloxy)-2,6-difluorobenzoic acid

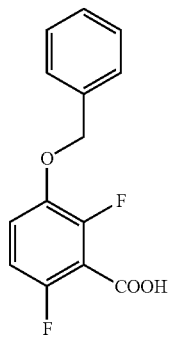 [SMILES: O=C(O)c1c(F)ccc(OCc2ccccc2)c1F]

To a 20 L 4-neck round bottom flask equipped with a mechanical stirrer, was charged THF (7.9 L, 10.0 vol.) and Di-isopropyl amine (474 g, 4680 mmol) under nitrogen atmosphere. The reaction mixture was cooled to 0 to −10° C., n-BuLi (1.6 M Solution in Hexane) (2.7 L, 4310 mmol.) was added slowly and stirred the mixture for 1 h at 0 to −10° C. The contents were cooled to −60 to −75° C., 1-(Benzyloxy)-2,4-difluorobenzene (790 g) solution in THF (3.95 L, 5.0 vo.) was added slowly drop wise at −60 to −75° C. and stirred for 1 h. Dry $CO_2$ gas was purged into the reaction mixture for 1.5 h at −55 to −75° C. The reaction completion was monitored by TLC. After reaction completion, the mass temperature raised to 0-20° C. and the pH 0-2 was adjusted with aqueous HCl solution (3.16 L, 4.0 vol.) water (2.4 L, 3.0 vol.) was added. The layers separated and aqueous layer was extracted with MDC. The organic layers combined and concentrated at below 50° C. under reduced pressure to give crude solid. The obtained crude was further purified by using base-acid treatment with 10% NaOH solution and followed by washing with 10% Ethyl acetate:Cyclohexane mixture (2.7 L, 3.7 vol.), filtered the product and dried at 60-65° C. for 8 h to give a pure product as white solid. (814 g, 85.86% yield). $^1$H NMR (300 MHz, DMSO-$d_6$) δ: 13.98 (bs, 1H), 7.33-7.47 (m, 6H), 7.10-716 (m, 1H), 5.20 (s, 2H). MS: 265.12 (M+1).

c. Preparation of 3-(Benzyloxy)-2,6-difluorobenzamide

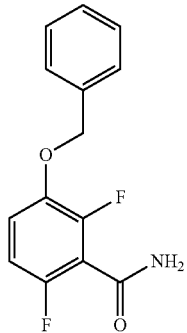 [SMILES: NC(=O)c1c(F)ccc(OCc2ccccc2)c1F]

To a 10 L 4-neck round bottom flask equipped with a mechanical stirrer, was charged 3-(Benzyloxy)-2,6-difluorobenzoic acid (800 g, 3027.66 mmol), DMF (80.0 mL, 0.10 vol.) and dry THF (2.4 L, 3.0 vol.) under nitrogen atmosphere. Thionyl chloride (540 g, 4538.95 mmol) was added slowly at 25-30° C. The reaction mixture was stirred for 4 h at 25-30° C. The reaction completion was monitored by TLC. After reaction completion, the reaction mixture was quenched in aqueous ammonia solution (8.0 L, 10 vol.) at below 20° C. and stirred for 2 h. The THF solvent was distilled completely at below 50° C. under reduced pressure. The precipitated solid was filtered & washed with water to give crude solid. The crude was purified by using 10% Ethylacetate:Cyclohexane (2.4 L, 3.0 vo.) mixture and dried at 60-65° C. for 8 h to give pure product as white solid. (735 g, 92.8% yield). $^1$H NMR (300 MHz, DMSO-$d_6$) δ: 8.14 (bs, 1H), 7.85 (bs, 1H), 7.25-7.47 (m, 6H), 7.03-7.09 (m, 1H), 5.15 (s, 2H).

d. Preparation of N-{[3-(Benzyloxy)-2,6-difluorophenyl]carbonyl}-1-methylpiperdine-4-carboxamide

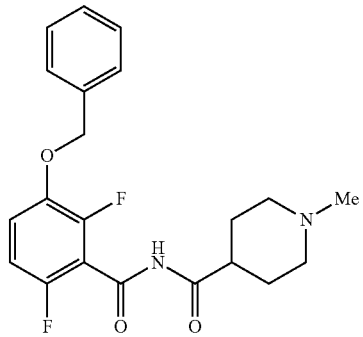 [SMILES: CN1CCC(C(=O)NC(=O)c2c(F)ccc(OCc3ccccc3)c2F)CC1]

To a 20 L 4-neck round bottom flask equipped with a mechanical stirrer, was charged 3-(Benzyloxy)-2,6-difluorobenzamide (733 g, 2784.4 mmol) and THF (7.33 L, 10.0 vol.) under nitrogen atmosphere. The contents were stirred for 10 min and cooled to 0-5° C., Sodium hydride (141.7 g, 5872.55 mmol, 60% dispersion in mineral oil) was added portion wise over 15 min at 0-10° C. Later N-Methylpiperdine acid chloride.HCl (2.0 eq.) was added slowly at 0-20° C. portion-wise and stirred for 30 min. The resulting mixture was stirred for 4 h at 25-30° C. The reaction completion was monitored by HPLC. After reaction completion, the contents were cooled to 0-5° C., water (7.3 L, 10.0 vol.) was added slowly at 0-10° C. and adjust the pH 1.0-2.0 with 1:1 aqueous HCl solution (2.2 L, 3.0 vol.) at 0-10° C. The layers were separated and the aqueous layer was washed with ethyl acetate (6.6 L, 9.0 vol.) and concentrated the organic volatiles under reduced pressure at below 50° C. Finally the solid was isolated by adjusting the pH 8.0-8.5 with 20% aqueous $Na_2CO_3$ solution at 25-30° C. The precipitated solid was filtered and washed with water to give final product as a white solid. (740 g, 68.42% yield). $^1$H NMR (300 MHz, DMSO-$d_6$) δ: 11.48 (bs, 1H), 7.33-7.47 (m, 6H), 7.11-7.14 (m, 1H), 5.19 (s, 2H), 2.74-2.78 (d, 2H), 2.50-2.51 (m, 1H), 2.13 (s, 3H), 1.72-1.87 (m, 4H), 1.48-1.53 (m, 2H).

e. Preparation of N-[(2,6-Difluoro-3-hydroxyphenyl)carbonyl]-1-methylpiperidine-4-carboxamide

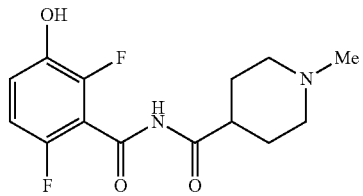 [SMILES: CN1CCC(C(=O)NC(=O)c2c(F)ccc(O)c2F)CC1]

To a 5 L autoclave, charged N-{[3-(Benzyloxy)-2,6-difluorophenyl]carbonyl}-1-methyl piperdine-4-carboxamide (350 g, 901.08 mmol), DMF (1.75 L, 10.0 vol.) and 5% wet Pd/C (52.5 g, 15% w/w) with Hydrogen pressure~0.5 Kg/Cm$^2$. The reaction mixture was stirred for 1 h at 25-30° C. The reaction completion was monitored by HPLC. After completion, reaction mixture was filtered through Hy-flo and cooled to 0-5° C. Water (8.4 L, 24.0 vol.) was added slowly to the reaction mixture at below 15° C. and the precipitated solid was filtered & dried for 8 h at 60-65° C. to give pure product as brown solid. (210.0 g, 78.36%). $^1$H NMR (300 MHz, DMSO-$d_6$) δ: 11.41 (bs, 1H), 6.92-6.95 (m, 2H), 2.73-2.79 (m, 2H), 2.39-2.44 (m, 1H), 2.14 (s, 3H), 1.73-1.87 (m, 4H), 1.53-1.57 (m, 2H). MS: 299.25 (M+1).

The intermediate compound 2-(chloromethyl)-6-(trifluoromethyl)[1,3]thiazolo[5,4-b]pyridine used in Example 1 was prepared as follows.

f. Preparation of 3-Nitro-2-thio-5-(trifluoromethyl)pyridine

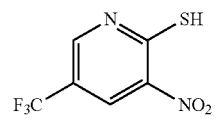

To a 5.0 L 4-neck round bottom flask equipped with a mechanical stirrer, was charged 2-Chloro-3-nitro-5-(trifluoromethyl)pyridine (400 g, 1765.69 mmol), Methanol (2.4 L, 6.0 vol.) and Thiourea (150.0 g, 1970 mmol) at 25-30° C. The reaction mixture was stirred for 4 h at 50-55° C. The reaction completion was monitored by HPLC. After completion, methanol from the reaction mixture was distilled out completely under reduced pressure at below 45° C. Water (2.0 L, 5.0 vol.) was added to the reaction mixture at 25-30° C. and followed by aqueous NaOH solution added slowly at 25-30° C. The aqueous layer was washed with Toluene and the product was precipitated by adjusting the pH 1-2 with 1:1 HCl solution at 0-5° C. The precipitate product was collected was filtered & dried to give the product as brown solid in good yield. (356.0 g, 90% yield). $^1$H NMR (300 MHz, DMSO-$d_6$) δ: 14.99 (bs, 1H,), 8.56-8.57 (s, 1H), 8.37 (s, 1H). MS: 223.13 (M-1).

g. Preparation of 3-Amino-2-thio-5-(trifluoromethyl)pyridine

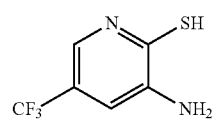

To a 5.0 L 4-neck round bottom flask equipped with a mechanical stirrer, was charged 3-Nitro-2-thio-5-(trifluoromethyl)pyridine (350 g, 1562.5 mmol), Iron powder (261.8 g, 4687.55 mmol), Ethylacetate (910 mL, 2.6 vol.) and water (910 mL, 2.6 vol.). Acetic acid (910 mL, 2.6 vol.) was added slowly at 25-30° C. The reaction mixture was stirred for 1 h at 65-70° C. The reaction completion was monitored by HPLC. After reaction completion, the reaction mixture was cooled to 25-30° C. & Ethyl acetate (1050 mL, 3.0 vo.) & water (1050 mL, 3.0 vol.) was added. The reaction mass was filtered through Hyflo bed and the layers were separated. The combined organic layer was washed with sodium bicarbonate, Water and sat. NaCl solution and the layers were separated. The organic layer was concentrated and the product was precipitated by using MDC (2 L, 5 vol) at 5-10° C. The solid isolated was filtered & dried to give final product as brown solid. (255.0 g, 84.15% yield). $^1$H NMR (300 MHz, DMSO-$d_6$) δ: 13.85 (bs, 1H), 7.41 (s, 1H), 6.82-6.83 (s, 1H), 6.16 (s, 2H). MS: 195.08 (M+1).

h. Preparation of 2-(Chloromethyl)-6-(trifluoromethyl)[1,3]thiazolo[5,4-b]pyridine

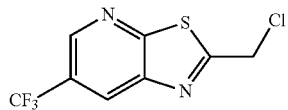 [SMILES: FC(F)(F)c1cnc2sc(CCl)nc2c1]

To a 5.0 L 4-neck round bottom flask equipped with a mechanical stirrer, was charged 3-Amino-2-thio-5-(trifluoromethyl)pyridine (245 g, 102.9 mmol) and Ethyl acetate (3.68 L, 15 vol.) at 25-30° C. The contents were cooled to 10-15° C. and Chloroacetyl chloride (287 g, 2542 mmol) was added slowly to the reaction mixture at 10-15° C. The reaction mixture was stirred for 15 h at 50-55° C. The reaction completion was monitored by HPLC. After reaction completion, water (1.225 L, 5.0 vol) was added slowly at 25-30° C. The organic layer was separated and washed with sodium bicarbonate, Water and sat. NaCl solution. The organic layer was concentrated & co-distilled with Isopropyl alcohol. The product was washed with Isopropyl alcohol (735 mL, 3.0 vol.) at 5-10° C., filtered & dried to give final product as brown solid. (265 g, 83.15% yield). $^1$H NMR (300 MHz, CDCl$_3$) δ: 8.88 (s, 1H), 8.47-8.48 (s, 1H), 4.96 (s, 2H). MS: 252.99 (M+1).

The intermediate compound N-methylpiperdine-4-carbonylchloride used in step d above was prepared as follows.

i. Preparation of N-Methylpiperdine-4-carbonylchloride

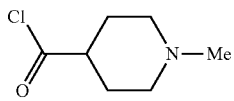

To a 1.0 L 4-neck round bottom flask equipped with a mechanical stirrer, was charged Thionyl chloride (300 mL, 3.0 vol.), N-Methylpiperdine acid.HCl (100 g, 556.6 mmol) under nitrogen atmosphere. The reaction mixture was heated for 1 h at 65-75° C. After the reaction completion the thionyl chloride was distilled out completely and co-distilled with Cyclohexane. Finally the product was washed with Cyclohexane, filtered and dried under nitrogen atmosphere as HCl salt (101 g, 92% yield).

Example 2 Preparation of Compound 1

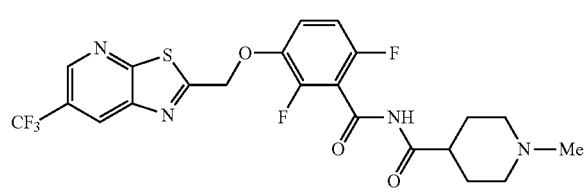

To a 100-mL round bottom flask equipped with a magnetic stirrer was charged with Compound J (1.0 g, 2.57 mmol, Compound 6 (1.0 g, 5.05 mmol), and THF (20 mL). With stirring NaH (600 mg, 15 mmol, 60% dispersion in mineral oil) was added portion wisely over 5 min. The resulting reaction mixture was stirred for 10 minutes, then a solution of water (40 µl) in THF (2 mL) was added via a pipet over 5 min. The reaction mixture changed from suspension to a brown solution. After completion of the reaction, it was quenched by the addition of few drops of water, and diluted with dichloromethane. The organic phase was separated, washed with brine and dried over Na2SO4. The solvent was removed in vacuo, and the resulting residue was purified by ISCO using 10% MeOH in DCM+1% NH4OH to afford a light brown solid, which was triturated with EtOAc to give a beige solid (590 mg, 44% Yield). 1H NMR (300 MHz, CDCl3) δ: 8.58 (s, 1H), 8.31 (broad s, 1H), 8.24 (s, 1H), 7.24-7.14 (m, 1H), 6.94-6.87 (m, 1H), 5.50 (s, 2H), 2.94-2.80 (m, 3H), 2.28 (s, 3H), 2.10-1.74 (m, 6H). 13C NMR (100 MHz, DMSO-d6) δ 174.9, 171.1, 161.2, 160.3, 153.5, 151.1, 149.1, 146.6, 144.5, 143.8, 141.8, 141.7, 127.8, 125.0, 124.1, 123.8, 123.5, 123.2, 122.3, 129.6, 117.6, 117.5, 115.9, 117.7, 115.6, 111.4, 111.1, 69.1, 54.8, 54.4, 45.9, 41.9, 27.6. HRMS calculated for C22H19F5N4O3S (M+H)+, 515.1171; found, 515.1181.

The intermediate compound j, 2,6-difluoro-3-((6-(trifluoromethyl)thiazolo[5,4-b]pyridin-2-yl)methoxy)benzamide, was prepared as follows.

a. Preparation of Compound j

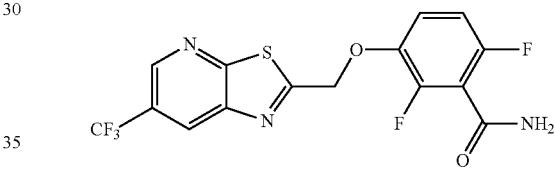

To 25 mL round bottom flask equipped with a magnetic stirrer, was charged 2-(chloromethyl)-6-(trifluoromethyl) thiazolo [5,4-b] pyridine (350 mg, 1.39 mmol), DMF (2.0 mL), NaHCO$_3$ (277 mg, 3.30 mmol), and 2,6-difluoro-3-hydroxybenzamide (230 mg, 1.32 mmol). The reaction mixture was stirred overnight at 50° C. The reaction completion was monitored by TLC. After reaction completion, the reaction mixture was cooled to ambient temperature (25-30° C.), water was added and the precipitated material was collected by filtration & dried to give a brown solid. After drying, the crude product was triturated with MDC to afford the desired product as light brown solid in good yield (380 mg, 71% yield). $^1$H NMR (300 MHz, DMSO-d$_6$) δ: 9.03-9.04 (s, 1H), 8.88-8.89 (s, 1H), 7.35-7.43 (m, 1H), 7.06-7.13 (m, 1H), 5.74 (s, 2H). MS: 390.10 (M+1).

Example 3 Preparation of Representative Salts

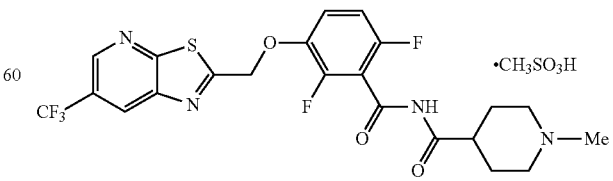

Preparation of TXA709. Mesylate: The TXA709 free base was dissolved in THF (1.5 L, 7.5 vol) and added Methane sulfonic acid (66 g, 686.78 mmol) at 35-40° C. The contents were stirred for 16 h at 25-30° C., cooled to 0-5° C. and stirred for 1 h and filtered to give crude as brown solid.

Purification of TXA709 Mesylate: To the solution of crude (TXA709 free base) dissolved in Acetone:Methanol (5.5: 7.0) mixture (2.5 L, 12.5 vol) at 55-65° C., activated carbon (0.5 g) was added, stirred for 15 min and filtered through Hy-flo in hot condition. The filtrate was cooled to 25-30° C., followed by further cooling to 0-5° C. The contents were stirred for 2 h, filtered and dried at 50-55° C. for 8 h to give pure product of TXA709.Mesylate as light brown solid. (114.0 g, 27.89% yield). $^1$H NMR (300 MHz, DMSO-$d_6$) δ: 11.74 (bs, 1H), 9.07 (s, 1H), 8.95 (s, 1H), 7.50-7.58 (m, 1H), 7.17-7.24 (m, 1H), 5.81 (s, 2H), 3.45-3.50 (d, 2H), 2.91-3.02 (m, 2H), 2.77-2.84 (d, 4H), 2.31 (s, 3H), 2.04-2.08 (d, 2H), 1.65-1.77 (m, 2H). MS: 515.08 (M+1).

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for preparing a compound of formula (I):

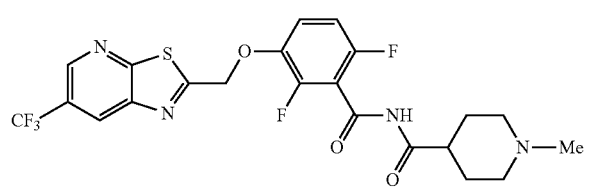
(I)

comprising reacting a phenol of formula e:

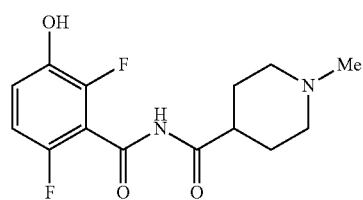
e with a chloride of formula h:

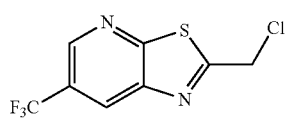
h to provide the compound of formula (I).

2. The method of claim 1 further comprising preparing the chloride of formula h by reacting the amino pyridine of formula g:

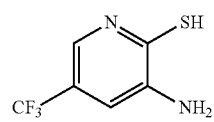
g with chloroacetic acid:

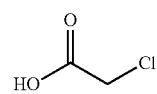

to provide the chloride of formula h.

3. The method of claim 2 further comprising preparing the amino pyridine of formula g by converting a corresponding nitro pyridine of formula f:

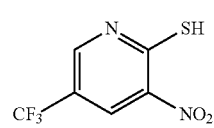
f to the amino pyridine of formula g.

4. The method of claim 3 further comprising preparing a nitro pyridine of formula f by reacting 2-chloro-3-nitro-5-(trifluoromethyl)pyridine with thiourea to provide the nitro pyridine of formula f.

5. The method of claim 1 further comprising preparing the phenol of formula e:

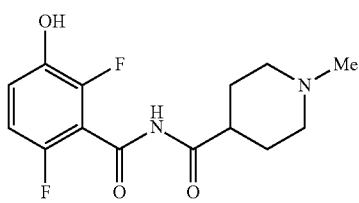
e by deprotecting the corresponding benzyl ether of formula d:

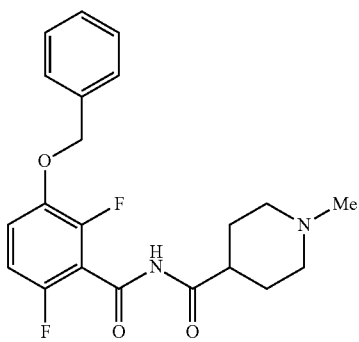
d to provide the phenol of formula e.

6. The method of claim 5 further comprising preparing the benzyl ether of formula d:

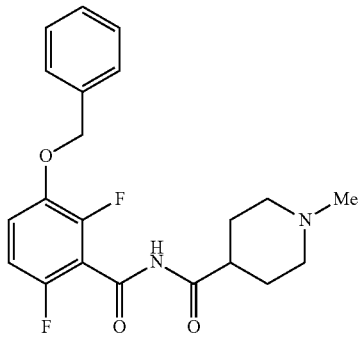

by coupling an acid chloride of formula i or a salt thereof:

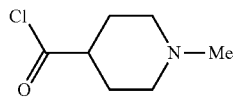

with an amide of formula c:

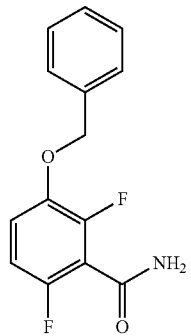

to provide the benzyl ether of formula d.

7. The method of claim 6 further comprising preparing the amide of formula c by converting an acid of formula b:

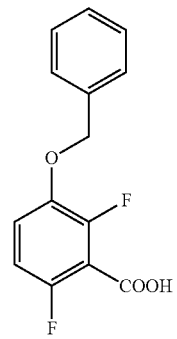

to the amide of formula c.

8. The method of claim 7 further comprising preparing the acid of formula b by converting a compound of formula a:

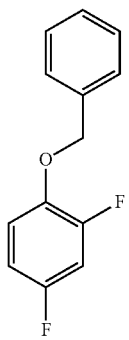

to the acid of formula b.

9. The method of claim 8 further comprising preparing the compound of formula a by converting a 2,4-difluorophenol to the compound of formula a.

* * * * *